United States Patent [19]

Müller

[11] 4,310,931

[45] Jan. 19, 1982

[54] HIP JOINT PROSTHESIS

[75] Inventor: Maurice E. Müller, Bern, Switzerland

[73] Assignees: Gebruder Sulzer A.G., Winterthur; Protek A.G., Bern, both of Switzerland

[21] Appl. No.: 191,413

[22] Filed: Sep. 29, 1980

[30] Foreign Application Priority Data

Oct. 11, 1979 [CH] Switzerland .................... 9217/79

[51] Int. Cl.³ .............................................. A61F 1/24
[52] U.S. Cl. ................................ 3/1.913; 128/92 CA
[58] Field of Search ................. 3/1.913, 1.912, 1.9; 128/92 CA, 92 C, 92 EC

[56] References Cited

U.S. PATENT DOCUMENTS

| | | | |
|---|---|---|---|
| 3,801,989 | 4/1974 | McKee | 3/1.912 |
| 3,814,089 | 6/1974 | Deyerle | 3/1.913 X |
| 3,829,904 | 8/1974 | Ling et al. | 3/1.912 |
| 3,939,498 | 2/1976 | Lee et al. | 3/1.913 |
| 4,141,088 | 2/1979 | Treace et al. | 3/1.912 |
| 4,199,824 | 4/1980 | Niederer | 3/1.913 |

FOREIGN PATENT DOCUMENTS 1409054 10/1975 United Kingdom ............... 3/1.913

*Primary Examiner*—Ronald L. Frinks
*Attorney, Agent, or Firm*—Kenyon & Kenyon

[57] ABSTRACT

To obtain an increase of the lateral distance between the longitudinal median axis of the straight prosthesis shank and the center of the joint head, the straight shank has a tapered medial side which changes over to an arcuate side on an arc of a circle which connects the transition point with the point of the smooth passage of the medial side into the prosthesis neck and with the center of the joint head. The angle between the longitudinal median axis and the prosthesis neck axis remains unchanged. This results in a lateral distance enlargement without having to shift the relative height position of the point at which the curved shank side meets the neck in the body, i.e., relative to the muscle origins.

4 Claims, 2 Drawing Figures

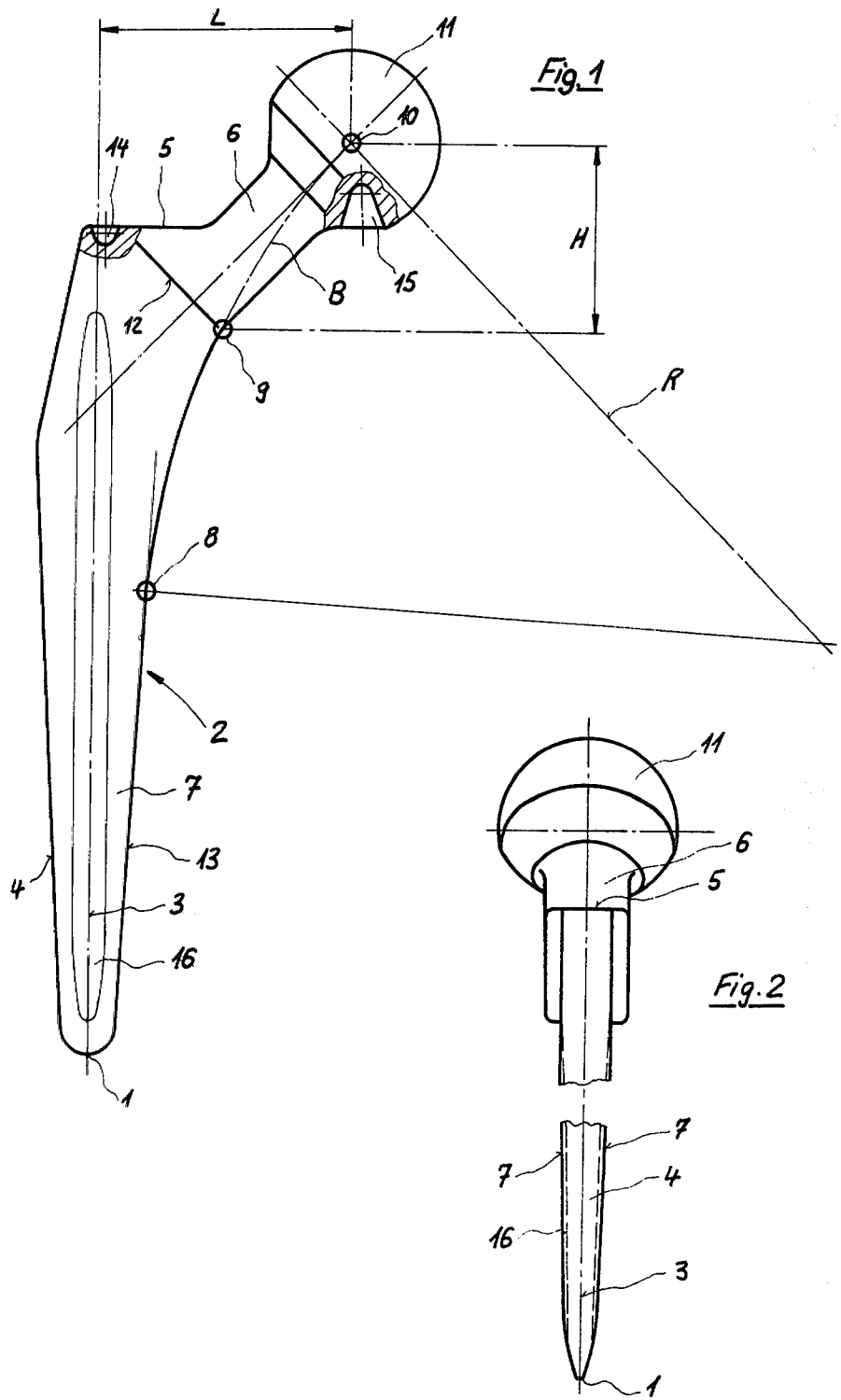

HIP JOINT PROSTHESIS

This invention relates to a hip joint prosthesis.

Heretofore, various types of prostheses have been known for implanting in femurs in order to form a hip joint. For example, hip joint prostheses have been formed with a straight blade type shank for anchoring as by a wedging action and through a cement bed in a femur. In some cases, the shank first widens conically from a free distal end symmetrically of a longitudinal median axis of the shank and then, at a point about three-quarters along the shank, bevels inwardly along the narrow lateral side towards the shank axis. The opposite narrow medial side, in these cases, passes along a smooth curve in stepless manner to a collar which separates the shank from a neck of the prosthesis.

Hip joint prostheses of a similar kind are known, for example from the journal "Orthopadie" 8 (1979), pages 73-74, and in particular FIG. 1. The so-called straight shank of this prosthesis is intended to be wedged in a hollow space of a medullary cavity, which has been surgically matched to the shank and filled with a bed of bone cement in such a way that the cement bed or cement quiver is largely relieved from carrying loads. The carrying support of this prosthesis takes place primarily by clamping along the narrow medial and lateral sides of the shank and by adaptation of the smooth curve of the medial narrow side to the calcarine arc situated medially in the femur. The point of transition of the narrow medial side into the prosthesis neck at the level of the sectional face of the surgical incision, which extends substantially perpendicular to the femur neck axis, then rests on the calcarine arc and thus establishes the height of the prosthesis in the body.

Generally, the adaptation of the straight shank, which can be implanted cementfree or with a cement quiver, to the individual patient has been achieved by providing a set of different shank sizes, which vary in shank length and/or in blade width of the shank. Although a great number of individually different cases can be covered, there is a need, at a constant angle between the longitudinal median axis and the prosthesis neck axis—in order not to increase the resulting load—and at a constant prosthesis height in the body (because of the adaptation to the origins of the muscles extending between pelvis and femur) to increase the lateral distance between the center of the prosthesis head and the longitudinal axis of the straight shank and to have a further possibility of variation for individual adaptation of the prosthesis shank to the diversities of individual patients. The longitudinal axis of the straight shank should essentially coincide with the longitudinal axis of the femur while the possibility of further variation allows a further improvement in the anchoring and the force transmission from the shank to the femur bone surrounding the shank.

Accordingly, it is an object of the invention to provide a hip joint prosthesis with a straight shank which can be adapted to patients having different lateral distances between a femur and a pelvic joint pan.

It is another object of the invention to eliminate a need to vary the shank length of a hip joint prosthesis to adapt to a femur.

Briefly, the invention provides a hip joint prosthesis which includes a shank for anchoring in a surgically prepared femur, a neck, a shoulder between the shank and neck and a joint head on the neck.

The shank has a narrow blade-like portion which is formed with a narrow lateral side and a narrow medial side and which extends along a longitudinal median axis from a distal end with a conical taper symmetrically of the axis. The shank also has a beveled side extending from a discontinuity on the lateral side at an angle inwardly toward the median axis and an arcuate side extending from a transition point on the medial side on a radius of a circle.

The neck is angularly disposed relative to the medial axis of the shank and has a lower edge connected to the arcuate side of the shank at a predetermined point. The shoulder extends from this latter point while the joint head has a center point disposed on an arc passing through the transition point, the center point and the predetermined point between the shank and neck. This arc further has a radius equal to the radius of the arcuate side of the shank.

In relation to other known hip joint prostheses, the prosthesis of the invention need only have the length of the neck changed to fit various patients. Thus, it is possible to shift a femur bone relative to a joint pan of a pelvis laterally without changing the angle of the longitudinal axis of the femur to the prosthesis neck axis and the height of the point at which the arcuate side of the shank meets the lower edge of the neck and, hence, that of the calcarine arc bracing the prosthesis, relative to the pelvis. By applying different radii for the circular arc in manufacturing a series of prostheses, it becomes possible to adjust, to a certain extent, the leg length resulting after one of these prostheses is inserted.

An improved transfer of the load stresses from the arcuate side of the narrow medial side of the prosthesis to the femur can be achieved by disposing the transition point of the shank taper below mid-height of the shank.

In order to obtain as correct as possible a fit of the prosthesis for each patient, the geometric adaptation of the prosthesis within narrow limits to the individual patient requires driving the straight shank with relatively great accuracy into an operatively enlarged medullary cavity of the femur. Therefore, in order to prevent tilting moments on the prosthesis shank while being driven in, a shoulder is formed between the lateral narrow side of the shank and the neck and a depression is disposed in the shoulder medially offset relative to the longitudinal median axis of the shank to receive a driving tool. The size of the medial offset, which may be up to 5 millimeters (mm), being generally 2 to 3 millimeters (mm).

If it is necessary, for example in case of alterations of the bone in the course of time, to replace the prosthesis by another similar one, the insertion of the second prosthesis will be greatly facilitated if the original cement quiver or the recess made by the first prosthesis in the medullary cavity remains intact to the extent possible when removing the first prosthesis. Therefore, it is advantageous to provide the prosthesis with a depression in the underside of the joint head for receiving a removing tool so as to establish a certain driving-out direction when the prothesis is being removed.

These and other objects and advantages of the invention will become more apparent from the following detailed description taken in conjunction with the accompanying drawings wherein:

FIG. 1 illustrates a front view of a hip joint prosthesis according to the invention; and FIG. 2 illustrates a side view of the prosthesis of FIG. 1 taken from the left.

Referring to FIGS. 1 and 2, the hip joint prosthesis has a shank 2 for anchoring in a cement bed (not shown) in a surgically prepared femur. As shown, the shank 2 has a longitudinal median axis 3 with a narrow blade-like portion extending from a distal end with a conical taper symmetrically of the axis 3. This portion defines a narrow lateral side 4 and a narrow medial side 13. At a level about ¾ up the shank 2, the lateral side 4 has a discontinuity from which a beveled side extends at an angle inwardly towards the axis 3 to terminate in an, at least, nearly horizontal shoulder 5 (i.e., the shoulder 5 is perpendicular to the axis 3). At a level below mid-height, the shank 2 has an arcuate side extending from a transition point 8 on a radius R from the medial side 13.

The prosthesis also has a neck 6 angularly disposed relative to the axis 3 of the shank 2. This neck 6 includes a lower edge which is connected to the arcuate side of the shank portion at a predetermined point 9 (see FIG. 1). Thus, the medial side 13 of the shank 2 is connected in a smooth stepless manner to the lower edge of the neck 6, while the shoulder 5 forms a transition from the shank 2 to the neck 6. In addition, the neck 6 carries a joint head 11 on the free end to receive a main load. This head 11 has a center point 10 disposed on a circular arc B passing through the points 8, 9, 10 and having a radius R equal to that of the arcuate side of the shank 2.

Referring to FIGS. 1 and 2, a shoulder 12 is disposed between the shank 2 and the neck 6 and extends from the point 9. As noted above, the point 9 is one of the singular fixed points for anchoring of the shank 2 in a femur.

The radius R is structurally determined by the lateral distance L which the center 10 of the joint head 11 is to have from the longitudinal median axis 3 and further by the height H which forms the desired vertical distance between points 9 and 10.

Referring to FIG. 1, a depression 14 for receiving a driving tool is provided on the shoulder 5 medially offset to the longitudinal median axis 3. The medial displacement of the depression 14 means that any tilting moments that may act on the shank as the shank is being driven in will be reduced to the extent possible. Also, any tilting moment which is exerted will be directed in the direction of the calcarine arc on the medial side of the femur. Thus, a firm hold of the steadily curved portion of the narrow side 13 on the bone is achieved.

A depression 15 is also provided on the underside of the joint head 11 for receiving a removal tool. Thus, a certain direction of removal can be maintained when removing the prosthesis.

Referring to FIG. 2, the blade sides 7 are provided with longitudinal grooves 16 and, at the distal end, are terminated by a circular transition from the lateral side 4 to the medial side 13, while coming to a point with relatively large radii (FIG. 2) in the perpendicular direction. The curvature of this end is chosen so that, to the extent possible, there is a steady transition of the loading forces from the shank 2 to the surrounding cement quiver and/or the bone tissue which may be compacted upon driving in of the prosthesis.

What is claimed is:

1. A hip joint prosthesis comprising
a shank for anchoring in a cement bed in a surgically prepared femur, said shank having a narrow blade-like portion formed with a narrow lateral side and a narrow medial side, and extending along a longitudinal median axis from a distal end with a conical taper symmetrically of said axis, a beveled side extending from a discontinuity on said lateral side at an angle inwardly toward said axis and an arcuate side extending from a transition point on said medial side on a radius of a circle;
a neck angularly disposed relative to said axis of said shank and having a lower edge connected to said arcuate side of said shank at a predetermined point;
a shoulder between said shank and said neck and extending from said predetermined point; and
a joint head on said neck having a center point disposed on an arc passing through said transition point, said predetermined point and said center point and having a radius equal to said radius of said arcuate side.

2. A hip joint prosthesis as set forth in claim 1 wherein said transition point is disposed below mid-height of said shank.

3. A hip joint prosthesis as set forth in claim 1 which further comprises a shoulder between said narrow lateral side and said neck and a depression in said shoulder medially offset from said longitudinal axis for receiving a driving tool.

4. A hip joint prosthesis as set forth in claim 3 which further comprises a depression in an underside of said joint head for receiving a removal tool.

* * * * *